(12) United States Patent
Castor et al.

(10) Patent No.: US 10,485,766 B2
(45) Date of Patent: Nov. 26, 2019

(54) DRUG DELIVERY SYSTEM AND METHOD FOR THE TREATMENT OF NEURO-DEGENERATIVE DISEASE

(71) Applicants: Aphios Corporation, Woburn, MA (US); Board of Supervisors of the Louisiana State University and Agricultural and Mechanical College, Shreveport, LA (US)

(72) Inventors: Trevor Percival Castor, Arlington, MA (US); Jonathan Steven Alexander, Shreveport, LA (US); Geoffrey Purdum, Hamilton, NJ (US); J. David Rios, Burlington, MA (US); Lisa M. Schrott, Decatur, GA (US); Theodore A. Tyler, Framingham, MA (US); Maria I. Vizcaino, New Haven, CT (US)

(73) Assignees: Aphios Corporation, Woburn, MA (US); Board of Supervisors of the Louisiana State University and Agricultural and Mechanical College, Shreveport, LA (US)

( * ) Notice: Subject to any disclaimer, the term of this patent is extended or adjusted under 35 U.S.C. 154(b) by 0 days.

(21) Appl. No.: 14/714,433

(22) Filed: May 18, 2015

(65) Prior Publication Data
US 2015/0246000 A1 Sep. 3, 2015

Related U.S. Application Data

(63) Continuation of application No. 13/720,157, filed on Dec. 19, 2012, now Pat. No. 9,034,347.
(Continued)

(51) Int. Cl.
*A61K 9/51* (2006.01)
*A61K 9/16* (2006.01)
(Continued)

(52) U.S. Cl.
CPC .............. *A61K 9/5153* (2013.01); *A61K 9/16* (2013.01); *A61K 9/4858* (2013.01); *A61K 31/365* (2013.01)

(58) Field of Classification Search
None
See application file for complete search history.

(56) References Cited

U.S. PATENT DOCUMENTS

| 4,560,774 A | 12/1985 | Pettit et al. |
| 4,611,066 A | 9/1986 | Pettit et al. |

(Continued)

FOREIGN PATENT DOCUMENTS

| WO | 2004/004641 A2 | 1/2004 |
| WO | 2009/129361 A2 | 10/2009 |
| WO | 2010/144499 A2 | 12/2010 |

OTHER PUBLICATIONS

Carpenter et al. (2008) "Endothelial PKC delta activation attenuates neutrophil transendothelial migration," Inflammatory Research. 57(5):216-229.
(Continued)

*Primary Examiner* — Carlos A Azpuru
*Assistant Examiner* — Casey S Hagopian

(57) ABSTRACT

Embodiments of the present invention are directed to the oral administration of Bryostatins for the treatment of neuro-degenerative disease.

5 Claims, 1 Drawing Sheet

Related U.S. Application Data

(60) Provisional application No. 61/577,426, filed on Dec. 19, 2011.

(51) Int. Cl.
*A61K 9/48* (2006.01)
*A61K 31/365* (2006.01)

(56) References Cited

U.S. PATENT DOCUMENTS

| | | | |
|---|---|---|---|
| 5,641,745 A * | 6/1997 | Ramtoola | A61K 9/1647 424/474 |
| 5,736,542 A | 4/1998 | Henry et al. | |
| 5,750,709 A | 5/1998 | Castor | |
| 5,854,064 A | 12/1998 | Castor et al. | |
| 6,221,153 B1 | 4/2001 | Castor et al. | |
| 6,228,843 B1 | 5/2001 | Dempsey | |
| 6,407,058 B1 | 6/2002 | Staddon et al. | |
| 6,624,189 B2 | 9/2003 | Wender et al. | |
| 9,034,347 B2 * | 5/2015 | Castor | A61K 9/16 424/400 |
| 2002/0061303 A1 | 5/2002 | Singh | |
| 2003/0171356 A1 | 9/2003 | Etcheberrigaray et al. | |
| 2003/0199469 A1 | 10/2003 | Schwartz et al. | |
| 2006/0165987 A1 | 7/2006 | Hildgen et al. | |
| 2007/0190163 A1 | 8/2007 | Malaknov et al. | |
| 2008/0004332 A1 * | 1/2008 | Alkon | A61K 31/00 514/423 |
| 2008/0207742 A1 | 8/2008 | Zohar et al. | |
| 2009/0270492 A1 * | 10/2009 | Wender | C07D 493/22 514/450 |
| 2009/0306225 A1 * | 12/2009 | Lichter | A61K 9/0046 514/772.1 |
| 2010/0166806 A1 | 7/2010 | Castor | |
| 2011/0129450 A1 | 6/2011 | Lazarov et al. | |
| 2012/0309818 A1 | 12/2012 | Alexander et al. | |
| 2015/0094363 A1 | 4/2015 | Alexander et al. | |
| 2015/0291616 A1 | 10/2015 | Castor | |
| 2015/0297555 A1 | 10/2015 | Castor | |

OTHER PUBLICATIONS

Dale et al., Comparison of effects of bryostatins 1 and 2 and 12-O-tetradecanoylphorbol-13-acetate on protein kinase C activity in A549 human lung carcinoma cells. Cancer Res. Jun. 15, 1989;49(12):3242-5.

Hale et al., The chemistry and biology of the bryostatin antitumor macrolides. Natural Product Reports. 2002;19 (4):413-453.

Healy et al. (2006) "Neutrophil transendothelial migration potential predicts rejection severity in human cardiac transplantation," European Journal of Cardio-thoracic Surgery. 29(5):760-766.

Joroan et al (1999) "The role of neutrophils in myocardial ischemia-reperfusion injury," Cardiovascular Research. 43(4):860-878.

Lopanik et al., Structure of bryostatin 20: a symbiont-produced chemical defense for larvae of the host bryozoan, Bugula neritina. J Nat Prod. Aug. 2004;67(8):1412-4.

Manning, Identifying byrostatins and potential precursors from the bryozoan Bugula neritina. Natural Product Research. 2005;19:467-491.

Mehla et al., Bryostatin modulates latent HIV-1 infection via PKC and AMPK signaling but inhibits acute infection in a receptor independent manner. PLoS One. Jun. 16, 2010;5(6):e11160. 15 pages.

Moreno et al. (2006) "Neovascularization in human atherosclerosis," Circulation. 113(18):2245-2252.

Pettit et al., Antineoplastic Agents 100. The Marine Bryozoan Amathia Convoluta. Tetrahedron. 1985;41(6):985-994.

Pettit et al., Antineoplastic agents. 340. Isolation and structural elucidation of bryostatins 16-18. J Nat Prod. Mar. 1996;59(3):286-9.

Pettit et al. Isolation and Structure of Bryostatin 1. J Am Chem Soc. 1982;104:6846-6848.

Pettit et al. Isolation and structure of bryostatin 9. J Nat Prod. Jul.-Aug. 1986;49(4):661-4.

Pettit et al. Isolation and Structure of Bryostatins 10 and 11. J Org Chem. 1987;52:2848-2854.

Pettit et al. Isolation and Structure of Bryostatins 12 and 13. J Org Chem. 1987;52:2854-2860.

Pettit et al. Isolation and Structure of Bryostatins 14 and 15. Tetrahedron. 1991;47(22):3601-3610.

Pettit et al. Isolation and structure of bryostatins 5-T Can J Chem. 1985;63:1204-1208.

Pettit et al., Structure of Bryostatin 4. An Important Antineoplastic Constituent of Geographically Diverse Bugula neritina (Bryoza). J Am Chem Soc. 1984;106:6768-6771.

Pettit et al., Structure of the Bugula neritina (Marine Bryozoa) Antineoplastic Component Bryostatin 3. J Org Chem. 1983;48:5354-5356.

Pettit et al., The Structure of Bryostatin 2 from the Marine Bryozoan Bugula Neritina. Journal of Natural Products. Jul.-Aug. 1983;46(4):528-531.

Stone et al., The Combination of All-Trans Retinoic Acid (Atra) and Bryostatin 1 (Bryo) Induces Monocytic Differentiation (Md) in Human Myeloid Leukemia Leukemia Research. 1997;21(1):S24, Poster Presentation No. 93. 1 page.

* cited by examiner

DRUG DELIVERY SYSTEM AND METHOD FOR THE TREATMENT OF NEURO-DEGENERATIVE DISEASE

RELATED APPLICATIONS

This application is a continuation of and claims priority to U.S. application Ser. No. 13/720,157, filed Dec. 19, 2012, and, claims priority to U.S. provisional application Ser. No. 61/577,426 filed Dec. 19, 2011, the entire contents of which is are incorporated by reference.

STATEMENT REGARDING FEDERAL SUPPORT

This invention was made with Federal support including National Institutes of Health Grant No. 1R44Ago34760-01A1.

FIELD OF INVENTION

Inventions of the present application are directed to the treatment of neuro-degenerative diseases such as Hutchinson Disease, Parkinson's disease, Down's syndrome and Alzheimer's disease.

BACKGROUND OF THE INVENTION

Neuro-de generative diseases, such as Alzheimer's disease, Hutchinson's Disease, Parkinson's disease, Kuru, Creutzfeldt—Jakob disease and other spongiform encephalopathies remain major health problems. Currently there are very limited means to treat these diseases. With respect to Alzheimer's, Hutchinson's and Parkinson's diseases, these diseases tend to manifest themselves in older individuals and as the diseases progress; the afflicted individuals are less able to care for themselves. It is therefore highly desirable to have simple therapies which can be administered (e.g. oral formulations) without the need for specially trained healthcare providers.

SUMMARY OF THE INVENTION

Embodiments of the present invention are directed to drug delivery systems, dosage forms and methods for the treatment of neuro-degenerative diseases. Turning first to embodiments directed to an article of manufacture, one embodiment features an effective amount of a Bryostatin-1 in a biopolymer. The biopolymer comprises a plurality of microspheres in which the spheres have a diameter between one to 1000 nanometers. The neuro-degenerative diseases which are the object of treatment in the present invention are exemplified by Alzheimer's disease, Hutchinson's Disease, Parkinson's disease, Kuru, Creutzfeldt—Jakob disease, Down's syndrome and spongiform encephalopathies.

As used herein, the term "a Bryostatin" refers to any and all Bryostatins and derivatives thereof. Twenty Bryostatins have been identified and certain examples feature a Bryostatin that is Bryostatin-1.

Embodiments of the present invention feature a biopolymer which is resistant to acid. For example, without limitation, one biopolymer is a poly (D, L-lactide-co-glycolic acid). This biopolymer has two components. Embodiments of the present invention feature a poly (D, L-lactide-co-glycolic acid) having a ratio of lactide and glycolic acid of 25-75% lactide with the remaining comprising glycolic acid. A common ratio is 50:50 lactide to glycolic acid as determined by weight. This biopolymer is resistant to gastric acid degradation and allows oral delivery of the drug to the small intestine for absorption.

Embodiments of the present invention feature spheres that are lyophilized for reconstitution in an aqueous solution. Another embodiment features spheres held in suspension for oral administration and/or held in an oral dosage form selected from the group of tablets, capsules, gel caps, and powders. Suspensions for oral administration are preferably flavored to improve patient acceptance.

A further embodiment of the present invention is directed to a method of treating neuro-degenerative disease. The method comprises the steps of administering an effective amount of a Bryostatin held in a plurality of spheres, each sphere comprising a biopolymer and Bryostatin, and each sphere having a diameter of one to 1000 nanometers.

Embodiments of the present method feature a Bryostatin selected from the group consisting of Bryostatins 1-20.

One embodiment of the present invention features a biopolymer which is resistant to acid. For example, without limitation, one acid resistant biopolymer is a poly (D, L-lactide-co-glycolic acid). Poly (D, L-lactide-co-glycolic acid) has a ratio of lactide and glycolic acid. A preferred ratio is 25-75% lactide with the remaining comprising glycolic acid.

Preferably, the microspheres are lyophilized for reconstitution in an aqueous solution, or held in suspension for oral administration or held in an oral dosage form selected from the group of tablets, capsules, gel caps, and powders.

As a further article of manufacture, embodiments of the present invention feature an effective amount of a Bryostatin dissolved in pharmaceutically acceptable oil for oral administration for the treatment of neuro-degenerative disease. As used herein, the term "pharmaceutically acceptable oil" refers to oils which are reasonably well tolerated for oral ingestion in small amounts of 5 to 10 milliliters. Embodiments of the present invention feature olive oil. Other embodiments comprise, by way of example, without limitation include, cotton seed oil, cod liver oil, castor oil, safflower oil, peanut oil, sesame oil, corn oil, vegetable oils, oils originating with animals, and other oils commonly used in the food industry. The oil is preferably administered in a gel cap.

An effective amount of Bryostatin for humans is about 0.1 to 3.0 mg per day in the pharmaceutically acceptable oil and approximately 100 micrograms to 2 mg per day as in the microsphere.

An effective amount of a Bryostatin dissolved in oil for oral administration for the treatment of neuro-degenerative disease, is approximately 3-10 ug per kilogram body weight per day.

A further embodiment of the present invention is directed to a method of treating neuro-degenerative disease comprising the steps of administering orally an effective amount of a Bryostatin dissolved in pharmaceutically acceptable oil.

Thus, as a treatment for neuro-degenerative diseases, embodiments of the present invention feature dosage forms and methods for the oral administration of an effective amount of a Bryostatin. These and other features and advantages of the present invention will be apparent upon reading the text of the detailed description below as well as viewing the accompanying drawings.

DETAILED DESCRIPTION OF THE INVENTION

Embodiments of the present invention will be described with respect to a drug delivery system, dosage form and method for the treatment of neuro-degenerative diseases exemplified by Alzheimer's disease, with the understanding that the discussion relates to other neuro-degenerative diseases as well. This discussion will feature the preferred embodiments of the invention with the understanding that features of the invention are capable of modification and alteration without departing from the teaching.

Figure 1:
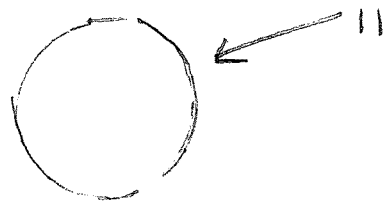
FIG. 1 depicts a microsphere embodying features of the present invention.

Turning first to FIG. 1, a microsphere, generally designated by the numeral 11 embodying features of the present invention is depicted. The microsphere 11, when combined with an adequate number of like microspheres comprises an effective dose of a Bryostatin in a biopolymer. Each microsphere 11 has a diameter of one to 1000 nanometers. Although depicted as a microsphere, the article of manufacture may have an irregular shape, roughness, or be filamentous in form.

As used herein, the term "a Bryostatin" refers to any and all Bryostatins and derivatives thereof. Examples of the present invention feature 'bryoids' which is a term that refers to a naturally occurring fractions of Bryostatins purified to about 95% chromatographic purity. Bryostatins are isolated in accordance with Castor, U.S. Pat. No. 5,750,709 and Castor "Supercritical fluid Isolation of Bryostatin-1, Phase II Final Report, SBIR Grant No. 5 R44 CA64017-03, Apr. 21, 2001.

Embodiments of the present invention feature a biopolymer resistant to acid. For the purpose of the present discussion, resistance to acid refers to stomach acids at a pH of approximately 1 to 3 for a period of time of about 0.5 to 4.0 hours. One biopolymer is a poly (D, L-lactide-co-glycolic acid). This biopolymer has two components, a lactide and a glycolic acid component. Embodiments of the present invention feature a poly (D, L-lactide-co-glycolic acid) having a ratio of lactide and glycolic acid of 25-75% lactide with the remaining comprising glycolic acid. A common ratio is 50:50 lactide to glycolic acid as determined by weight. This biopolymer is resistant to acid degradation and allows oral delivery of the drug to the small intestine for absorption.

Embodiments of the present invention feature microspheres that are lyophilized for reconstitution in an aqueous solution. Another embodiment features microspheres held in suspension for oral administration and/or held in an oral dosage form selected from the group of tablets, capsules, gel caps, and powders. Methods of making tablets, capsules, gel caps and powders are well known in the art. (Remington, 'The Science and Practice of Pharmacy'—20$^{th}$ Edition Lippincott, Williams and Williams). Suspensions for oral administration are preferably flavored to improve patient acceptance.

Another embodiment of the present invention features pharmaceutically orally acceptable oil containing an effective amount of Bryostatin. An amount of oil for administration is determined, and an effective amount of Bryostatin is dissolved in such oil in a manner known in the art. Preferably, the amount of oil which is intended for oral administration is enclosed in a gel cap in a manner known in the art. For example, Vitamin D and Vitamin E supplements are often enclosed in gel cap formulations.

Figure 2:
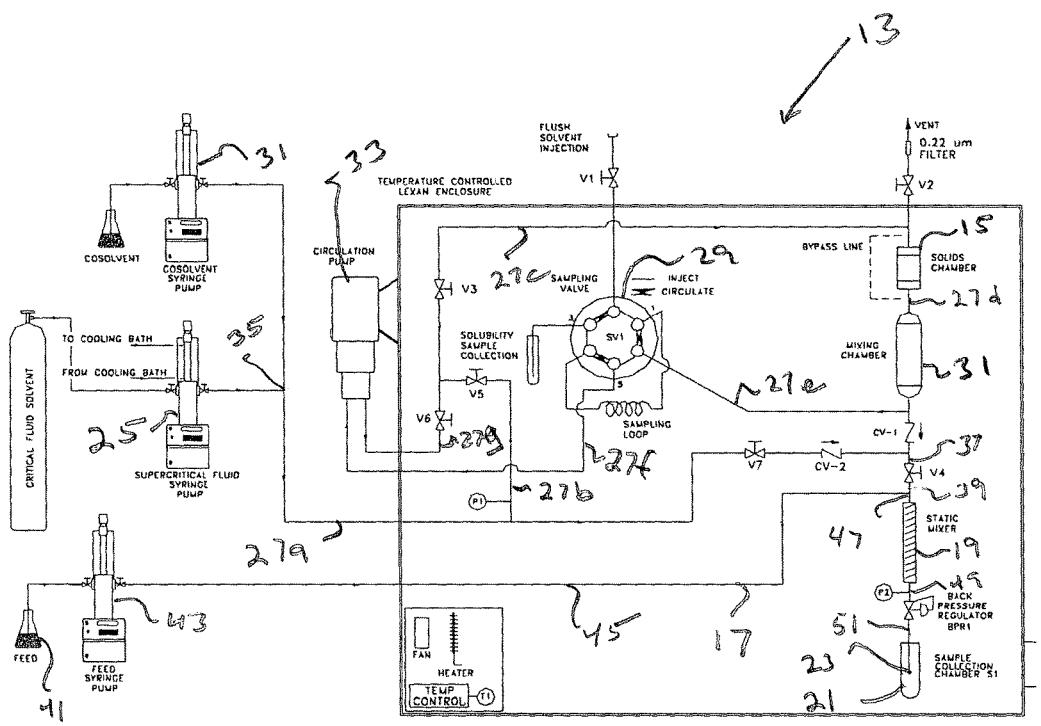
FIG. 2 depicts an apparatus for making one or more microspheres of the present invention.

The present method and apparatus will be described with respect to FIG. 2 which depicts in schematic form a polymer sphere apparatus, generally designated by the numeral 13. The polymer sphere apparatus is comprised of the following major elements: a polymer vessel 15, a Bryostatin drug injection assembly 17, an admixture chamber 19, a depressurization vessel 21, and an orifice nozzle 23.

Polymer vessel 15 is in fluid communication with a supercritical critical or near critical syringe pump 25 via conduits 27a, 27b and 27c. Supercritical, critical or near critical pump 25 is in fluid communication with a source of supercritical, critical or near critical fluid.

Polymer vessel 15 is also in fluid communication with a modifier syringe pump 31 via conduit 33 which intersects with conduit 27a at junction 35. Modifier syringe pump 31 is in communication with a source of modifiers and/or entrainers (not shown).

Polymer vessel 15 is loaded with polymer. This polymer vessel receives supercritical, critical or near critical fluid from supercritical critical or near critical pump 25 via conduits 27a, 27b and 27c. Polymer vessel 15 receives modifiers and/or entrainers from modifier pump 31 via conduit 33. Polymer is dissolved in the supercritical, critical or near critical fluid and modifier to form a polymer solution. Formation of the polymer solution is facilitated by circulating the polymers and supercritical, critical or near critical fluid in a loop with a conduits 27d, 27d, 27e, 27f, and 27g, a master valve 29, a static mixer 31, and a circulation pump 33.

Polymer vessel 15 is in fluid communication with admixture chamber 19 via conduits 37 and 39. Admixture chamber 19 is also in fluid communication with Bryostatin drug injection assembly 17. Bryostatin drug injection assembly 17 comprises Bryostatin drug syringe pump 43, a source of a Bryostatin 41 and conduit 45. Bryostatin drug syringe pump 43 is in communication with a source of Bryostatin material and pressurizes and compels such material through conduit 45. Conduit 45 is in communication with admixture chamber via conduits 39 which intersects conduit 45 at junction 47. Preferably, junction 47 is a mixing "T".

Admixture vessel 19 is in the nature of an inline mixer and thoroughly mixes incoming streams from the polymer vessel 15 and Bryostatin drug injection assembly 17. Admixture vessel 19 is in communication with orifice nozzle 23 via conduit 49. Orifice nozzle 23 is in the nature of a back pressure regulator and has a nozzle defining one or more orifices which discharge into depressurization vessel 21 via conduit 51. Preferably orifice nozzle 23 controls pressure and decompression rates such that a supercritical critical or near critical carbon dioxide enters the orifice at a rate of about 0.425 mls/min and 0.075 mls/min acetone or about 0.5 mls/min carbon dioxide and ethanol combined to maintain system pressure at 2,500 psig.

The operating pressure of the system can be preset at a precise level via a computerized controller (not shown) that is part of the syringe pumps. Temperature control in the system is achieved by enclosing the apparatus 11 in ¼" Lexan sheet while utilizing a Neslab heating/cooling system coupled with a heat exchanger (not shown) to maintain uniform temperature throughout the system.

In a typical experimental run, polymeric materials were first packed into the polymer vessel 15. Supercritical critical or near critical fluid and an ethanolic solution of Bryostatin drug were charged into the supercritical, critical or near critical syringe pumps 25 and 31, respectively, and brought to the desired operating pressure. In the alternative, an ethanol solution of Bryostatin drug is charged into bioactive syringe pump 43.

The system is pressurized with the supercritical critical or near critical fluid via supercritical, critical or near critical syringe pump 25 to the pressure level equal to that set in modifier syringe pump 31 and Bryostatin drug syringe pump 43, and maintained at this level with the nozzle orifice 23. The dynamic operating mode for all pumps is set so that each pump can be operated at its own desired flow rate. The supercritical critical or near critical stream flows through the polymer vessel 15, dissolves polymer and contacts the Bryostatin drug stream at junction 47. The mixture of supercritical critical nears critical fluid, Bryostatin drug and polymer materials is then passed through admixture chamber 19 for further mixing. Finally, the mixed solution entered orifice nozzle 23 and was injected into a 10% sucrose solution containing 0.1% polyvinyl alcohol, 40% ethanol with trace acetic acid in the depressurization vessel 21. As a result of supercritical fluid decompression, polymer spheres containing Bryostatin drug are formed in the 10% sucrose solution, 0.1% polyvinyl alcohol, 40% ethanol with trace acetic acid. The expanded supercritical fluid exits the system via a vent line on the depressurization vessel 21.

The polymer spheres are in the nature of microspheres 11. These microspheres 11 are frozen at −80° degrees Centigrade and lyophilized.

Oil based Bryostatin solutions are dissolved in olive oil with vitamin E as a preservative and lecithin and medium chain triglyceride emulsifiers to increase bioavailability. The oil with the dissolved Bryostatin is encapsulated in gel capsules with a nitrogen purge and head. In the alternative, the oil with dissolved Bryostatin is administered as a liquid dosage form. However, those skilled in the art recognize that oily formulations are not normally well received due to taste and texture. The oil with dissolved Bryostatin may also be emulsified and administered as a liquid formulation. Emulsification may mask some of the less desirable taste and texture associated with oil based oral formulations.

Examples

Bryostatin Microspheres

Microspheres comprising polymers and Bryostatin 1 were prepared in accordance with the methods described above. The results are summarized in Table 1 below.

The nanospheres appear stable at 4-25° C. (Centigrade) for at least one week duration. Further, the nanospheres appear stable in solutions at about pH 1.13 at 37° C. (Centigrade), similar to a stomach environment.

Results further suggest that nanospheres with Bryostatins and Bryostatin 1, in particular, induce alpha-secretase processing of amyloid precursor protein (APP) to s-APP alpha, and activate protein kinase C (PKC) isoforms alpha, delta and epsilon (measured by membrane translocation) in the SH-SY5Y neuroblastoma cell line. These events are well-described cell and pharmacological events associated with prevention of beta-secretase mediated formation of beta-amyloid, the presumptive cause of dementia in human Alzheimer's disease and in the sweAPP/PS1 mouse model of Alzheimer's disease.

Oil-Based Formulations for Liquid-Fill Gel Capsules

Based on the hydrophobicity of Bryostatin-1, we developed an oil-based formulation of Bryostatin-1.

A stock solution of 82 mg/100 mL of Bryostatin-1 was used. Isopropyl alcohol, Extra Virgin olive oil, sesame oil, and vegetable oil were all used as solvents.

Thirty microliters of the stock solution were placed in each of 4 clean, dry HPLC vials. The ethanol was allowed to evaporate, leaving 25 micrograms in the vial. Then, 1.0 mL of the solvent was placed in the vial and vortexed to ensure proper mixing. These samples were then injected on a normal phase HPLC system, with a gradient of 10%-70% isopropyl alcohol in hexane as the mobile phase (specifically developed for this experiment).

The concentration of each vial theoretically should be 2.5 mg/100 mL. The results are listed in Table 2.

TABLE 2

Concentrations of Bryostatin in Different Solvents

| Solvent | Concentration (mg/100 mL) |
|---|---|
| Isopropyl Alcohol | 2.6035 |
| Extra Virgin Olive Oil | 2.9945 |
| Vegetable Oil | 2.5475 |
| Extra Virgin olive containing mixed natural tocopherol antioxidants to improve stability, and lecithin and medium chain triglyceride emulsifiers to increase bioavailability. | 2.4431 |

TABLE 1

Summary of Polymer Nanoencapsulation of Bryostatin-1 Experiments

| Expt. No. | SFS | P (bars) | T (° C.) | Particle Size (nm) | Bryo-1 (mg/100 mls) | Encapsulation (%) |
|---|---|---|---|---|---|---|
| ALZ-01-01 | $CO_2$:Acetone::95:5 | 171 | 45 | 259 | 0.0511 | 11.4 |
| ALZ-02-01 | Freon-22 | 205 | 22 | 973 | 0.3089 | 16.8 |
| ALZ-03-01 | $CO_2$:Ethanol::85:15 | 171 | 45 | 246* | 0.0027 | 71.3 |
| ALZ-04-01 | $CO_2$:Acetone::95:5 | 171 | 45 | 215* | 0.0160 | 50.8 |
| ALZ-05-01 | $CO_2$:Acetone::95:5 | 171 | 45 | 254* | 0.1323 | 84.0 |
| ALZ-06-01 | $CO_2$:Acetone::85:15 | 171 | 45 | 251* | 0.2374 | 82.3 |

*After lyophilization and reconstitution

The data in Table 2 indicates that Bryostatin-1 is soluble in a variety of different types of oil. The reason for the higher concentrations than the standard (isopropyl alcohol) is due to the baseline. While attempting a baseline subtraction for each oil, there was negative absorbance so the blank IPA sample was subtracted from each sample's baseline. While this incorporates a little more area for integration, the amount of Bryostatin in the oil was quantifiable. In addition, the sesame oil had an integration area that was much larger than the peak itself. When manipulating the review application within the Millennium HPLC software, it was seen that the peak itself had a similar area to that of the standard (Bryostatin in IPA).

Bryostatin-1 is soluble in a variety of oils, with the best results in Extra Virgin Olive Oil, Vegetable Oil, and Extra Virgin Olive Oil with excipients. Bryostatin-1 is formulated to a specific concentration in Extra Virgin olive containing mixed natural tocopherol antioxidants to improve stability, and lecithin and medium chain triglyceride emulsifiers to increase bioavailability. This formulation is then encapsulated in gel capsules with a $N_2$ purge and head. Targeted concentrations are in the range of 10 to 25 µg/mL.

Water Maze Studies

Mouse strain B6C3-Tg carrying mutant Swedish Amyloid precursor protein (sweAPP) and PS1 (presenilin-1) genes associated with early onset Alzheimer's disease were subjected to water maze tests at 5-6 months of age. These tests suggest that mice that received Bryostatin-1 at a dose of 5 micrograms/mouse on alternative days orally in an oil 20 formulation showed significant protection against Alzheimer's disease mediated memory loss produced by the APP/PS1 mutations as compared with memory acquisition skills seen in control animals.

Therefore, we have described the present invention with respect to preferred embodiments with the understanding that these embodiments are capable of modification and alteration without departing from the teaching herein. Therefore, the present invention should not be limited to the precise details, but should encompass the subject matter of the claims that follow.

The invention claimed is:

1. A method of treating neuro-degenerative disease comprising orally administering to a patient in need thereof an effective amount of a Bryostatin held in a plurality of microspheres, wherein said Bryostatin is selected from the group consisting of Bryostatins 1-20, wherein each of said microspheres comprises a polymer and the Bryostatin, and wherein said microspheres have a diameter of one to 1000 nanometers, wherein the polymer consists of a poly(D,L-lactide-co-glycolic acid), and wherein the microspheres are held in an oral dosage form selected from the group of a suspension, tablets, capsules, gelatin capsules and powders.

2. The method of claim 1 wherein said poly (D, L-lactide-co-glycolic acid) has a ratio of lactide to glycolic acid to be 25-75% lactide with the remaining comprising glycolic acid.

3. The method of claim 1 wherein said microspheres are lyophilized for reconstitution in an aqueous solution.

4. The method of claim 1 wherein said effective amount of Bryostatin is approximately 3-10 µg per kilogram body weight per day.

5. The method of claim 1 wherein the polymer is resistant to acid.

* * * * *